(12) United States Patent
Kinnunen et al.

(10) Patent No.: US 12,733,914 B2
(45) Date of Patent: Sep. 15, 2026

(54) KIT FOR HOLDING SAMPLE

(71) Applicant: Summa Finland Oy, Oulu (FI)

(72) Inventors: Tommi Kinnunen, Helsinki (FI); Paavo Pietola, Helsinki (FI); Marko Mäkinen, Oulu (FI); Heikki Keränen, Oulu (FI)

(73) Assignee: Summa Finland Oy, Oulu (FI)

( * ) Notice: Subject to any disclaimer, the term of this patent is extended or adjusted under 35 U.S.C. 154(b) by 304 days.

(21) Appl. No.: 18/429,527

(22) Filed: Feb. 1, 2024

(65) Prior Publication Data

US 2024/0268799 A1 Aug. 15, 2024

(30) Foreign Application Priority Data

Feb. 15, 2023 (FI) .................................... 20235164

(51) Int. Cl.
*A61B 10/00* (2006.01)
*A61B 50/31* (2016.01)
*B65D 81/18* (2006.01)

(52) U.S. Cl.
CPC .......... *A61B 10/0096* (2013.01); *B65D 81/18* (2013.01); *A61B 2050/311* (2016.02)

(58) Field of Classification Search
CPC .......... A61B 10/0096; A61B 2050/311; B65D 81/15; F25D 3/08; F25D 2331/0814; F25D 2303/0832
USPC ............ 206/364, 472–475, 583, 592, 459.5; 62/457.1, 457.5, 371
See application file for complete search history.

(56) References Cited

U.S. PATENT DOCUMENTS 4,429,793 A * 2/1984 Ehmann ................ A61M 5/003 62/457.2
4,884,684 A * 12/1989 Bernardin .......... B65D 81/1075 206/592
6,935,133 B2 * 8/2005 Keeter .................. A61M 5/003 62/457.2

(Continued)

FOREIGN PATENT DOCUMENTS

CN 216333543 U 4/2022
EP 2494293 B1 9/2012

(Continued)

OTHER PUBLICATIONS

Finnish Patent and Registration Office, Search Report, Application No. 20235164, Mailed Aug. 29, 2023, 2 pages.

*Primary Examiner* — Chun Hoi Cheung
(74) *Attorney, Agent, or Firm* — Ziegler IP Law Group, LLC.

(57) ABSTRACT

Disclosed is a kit for holding samples with a casing having a first portion and a second portion. When the kit is in enclosed state, the first and second portions define closed space therebetween. A mattress having first part and second part holds a refrigerant therein. A temperature of the refrigerant lies within a predefined range of temperature. Stencil(s) having openings of a first type are dimensioned to receive containers therein and to hold containers securely. Each container is capable of holding a sample therein. When the kit is in an enclosed state, the stencil(s) is encased by first and second parts, thereby enabling temperature of samples held in containers to be maintained within predefined range of temperature.

15 Claims, 4 Drawing Sheets

(56) References Cited

U.S. PATENT DOCUMENTS

| | | | | |
|---|---|---|---|---|
| 8,763,423 | B2 * | 7/2014 | Tattam | B65D 88/528 62/457.2 |
| 8,938,986 | B2 * | 1/2015 | Matta | F25D 3/06 62/530 |
| 9,072,653 | B2 * | 7/2015 | Nemard | B65D 25/102 |
| 9,267,722 | B2 * | 2/2016 | Blezard | B65D 81/3813 |
| 9,284,095 | B2 * | 3/2016 | Caruth | A61B 50/13 |
| 10,045,597 | B2 * | 8/2018 | Caruth | A45C 15/00 |
| 10,842,712 | B1 * | 11/2020 | Wingate, III | A61J 1/03 |
| 11,692,762 | B2 * | 7/2023 | Waltermire | B65D 81/3888 206/545 |
| 2008/0111685 | A1 * | 5/2008 | Olson | G08B 3/10 340/568.1 |
| 2008/0141700 | A1 * | 6/2008 | Fuchs | F25D 3/08 206/570 |
| 2010/0064698 | A1 * | 3/2010 | Schabron | F25D 3/08 62/62 |
| 2013/0037428 | A1 * | 2/2013 | Wingate, III | A61J 1/03 206/223 |
| 2013/0291584 | A1 * | 11/2013 | Chapman, Jr. | F25D 3/08 62/371 |
| 2014/0157797 | A1 * | 6/2014 | Kovalick | F25D 3/06 62/371 |
| 2020/0079570 | A1 | 3/2020 | Kitano et al. | |

FOREIGN PATENT DOCUMENTS

| | | | |
|---|---|---|---|
| FR | 2850364 | A1 | 7/2004 |
| JP | S6151568 | A | 3/1986 |
| WO | 2022129544 | A1 | 6/2022 |

* cited by examiner

KIT FOR HOLDING SAMPLE

TECHNICAL FIELD

The present disclosure relates to kits for holding samples.

BACKGROUND

Storage kits are widely used for careful storage of samples in laboratories and other similar facilities. The samples may be, fluids such as bodily fluids, vaccines, reagents, biological specimen and their derivatives. Storage of samples at desired temperature is necessary in order to maintain physical and/or chemical properties of the samples and/or to utilize those samples in future, such as for experimentations, laboratory testing, and the like. There are various solutions provided for storing the samples. However, conventional storage kits are sub-optimal and do not provide desired results.

Notably, conventional storage kits are unable to maintain a required temperature of samples. This is often due to reasons such as wrongful or suboptimal placement of temperature regulation materials (for example, such as ice, liquid bath, and similar) with respect to the samples, undesirable movement of the samples and/or the temperature regulation materials when the kit is transported from one place to another, and similar. For example, some of the conventional storage kits may be unable to maintain the samples at temperatures lower than 0 degrees Celsius for several hours. The aforesaid limitations of the conventional storage kits may lead to spillage and/or change in physical and/or chemical properties of the samples which is undesirable.

Therefore, in light of the foregoing discussion, there exists a need to overcome the aforementioned drawbacks associated with the conventional storage kits.

SUMMARY

The present disclosure seeks to provide a kit for holding samples. An aim of the present disclosure is to provide a solution that overcomes at least partially the problems encountered in prior art.

In one aspect, an embodiment of the present disclosure provides a kit for holding samples, the kit comprising:

- a casing having a first portion and a second portion, wherein when the kit is in an enclosed state, the first portion and the second portion define a closed space therebetween;
- a mattress having at least a first part and a second part, wherein the first part and the second part of the mattress are accommodated in the first portion and the second portion of the casing, respectively, wherein when the kit is in use, the mattress holds a refrigerant therein, a temperature of the refrigerant lies within a predefined range of temperature, and wherein the mattress is deformable such that its deformability depends on the temperature of the refrigerant; and
- at least one stencil having a plurality of openings of a first type, wherein the plurality of openings of the first type are dimensioned to receive a plurality of containers therein and to hold the plurality of containers securely, each container being capable of holding a fluid therein and being closed at its first end, wherein when the kit is in the enclosed state, the at least one stencil is encased by the first part and the second part, thereby enabling a temperature of the samples held in the plurality of containers to be maintained within the predefined range of temperature.

Embodiments of the present disclosure substantially eliminate or at least partially address the aforementioned problems in the prior art, and enable safe storage and transportation of samples while maintaining the samples within the predefined range of temperature.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
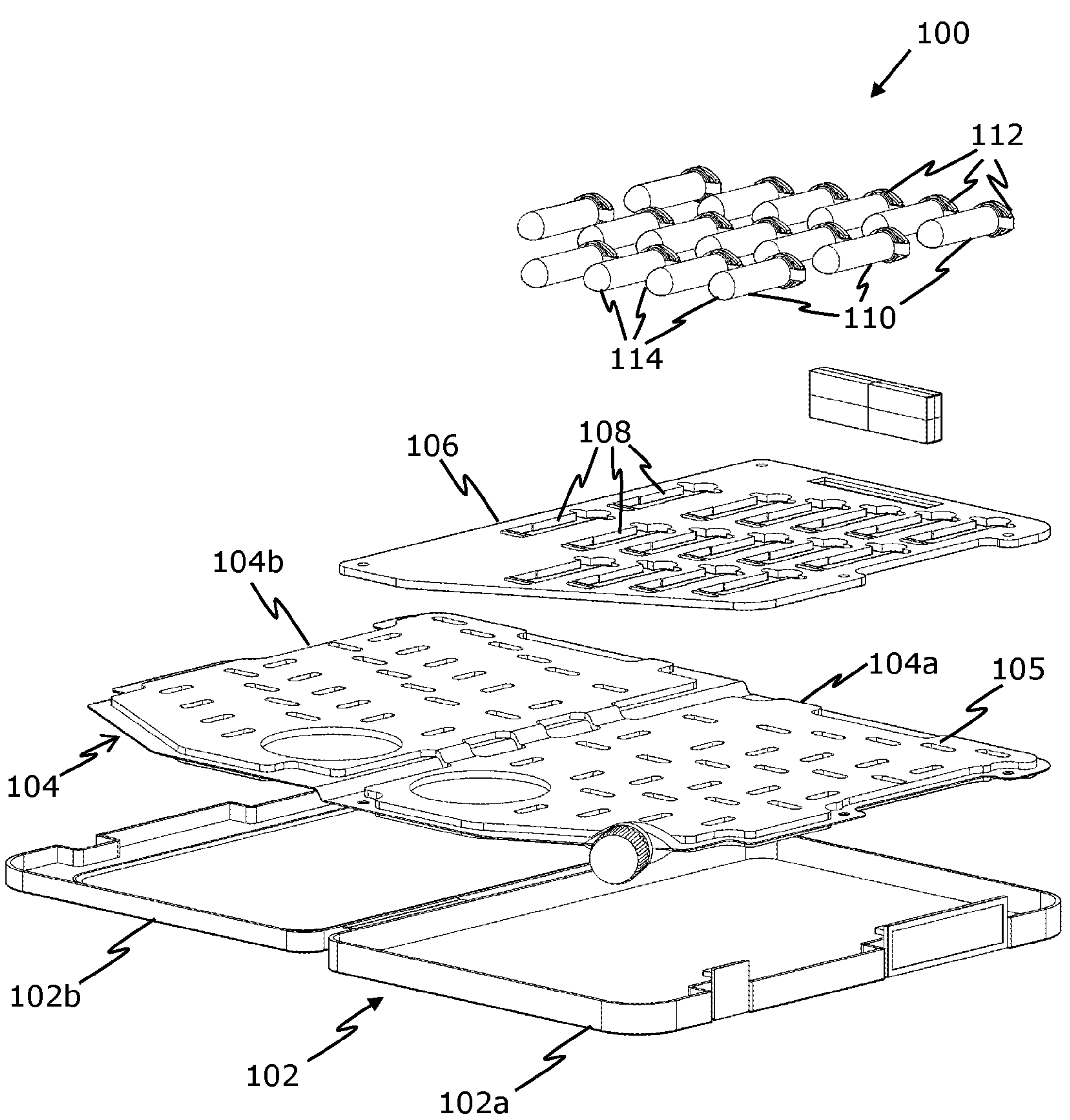
FIG. 1 is an exploded view of a kit for holding samples, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a kit for holding samples, the kit comprising:

a casing having a first portion and a second portion, wherein when the kit is in an enclosed state, the first portion and the second portion define a closed space therebetween;

a mattress having at least a first part and a second part, wherein the first part and the second part of the mattress are accommodated in the first portion and the second portion of the casing, respectively, wherein when the kit is in use, the mattress holds a refrigerant therein, a temperature of the refrigerant lies within a predefined range of temperature, and wherein the mattress is deformable such that its deformability depends on the temperature of the refrigerant; and at least one stencil having a plurality of openings of a first type, wherein the plurality of openings of the first type are dimensioned to receive a plurality of containers therein and to hold the plurality of containers securely, each container being capable of holding a sample therein and being closed at its first end, wherein when the kit is in the enclosed state, the at least one stencil is encased by the first part and the second part, thereby enabling a temperature of the samples held in the plurality of containers to be maintained within the predefined range of temperature.

The present disclosure provides the kit for holding samples. The temperature of a sample held in a given container is maintained within the predefined range of temperature due to the mattress covering the given container (arranged in the at least one stencil) from both sides. Maintaining the temperature of the samples within the predefined range of temperature is essential in order to preserve physical and/or chemical properties of the samples so as to effectively use the samples (for example, for experimental purposes) in future. More beneficially, the aforesaid arrangement of the plurality of containers in the kit provides a firm and/or secure grip for the plurality of containers, so as to avoid displacement of the plurality of containers. Moreover, owing to the presence of the refrigerant having the temperature lying within the predefined range, movement of the plurality of containers in the kit is restricted. Further, the kit is light weight, easy to open and close, and is cost-friendly.

Throughout the present disclosure, the term "kit" refers to a storage apparatus for the samples. Herein the "sample" of a substance refers to a small quantity of the substance. The samples could be fluidic samples, semi-solid samples, solid samples. Optionally, the samples comprise a plurality of: a body fluid, a dosage of a medicine, a vaccine, a reagent. Examples of the body fluid include, saliva, blood, urine, and the like. Examples of the semi-solid samples include, stool samples, mucus, and the like. Examples of the solid samples include, medicines, pellets, and the like.

The term "casing" refers to an outermost component of the kit which acts as an enclosure and overall protective body that houses other components of the kit. In other words, the casing is a solid structural component used to hold and enclose other components, such as the mattress, the at least one stencil, and similar.

The "enclosed state" of the kit is that state of the kit in which the first portion and the second portion of the casing are joined with each other to form the closed space therebetween. The kit may be maintained in the enclosed state during transportation, storage, or similar. In the enclosed state, the plurality of containers are not accessible.

The casing may be manufactured in any shape and size, depending upon a requirement. For example, shapes of the casing may depend on geometry and types of the plurality of containers, a number of the plurality of containers, an arrangement of the plurality of containers, and similar. The first portion and the second portion of the casing have three-dimensional (3D) geometries which enable the kit to have a corresponding 3D shape. The first portion and the second portion may be transparent or translucent. A material used to manufacture the first portion and the second portion is lightweight, has high durability, and high strength. Optionally, the first portion and the second portion of the casing is manufactured using at least one of: a polypropylene material, a polyethylene material, a glass, a metal material, a freezer-safe material. In an example, the casing may have glossy finish.

In an embodiment, the first portion and the second portion are integrated (i.e., physically joint) with each other. In such a case, the casing is manufactured as a single element having two portions that are joint together. In another embodiment, the first portion and the second portion are physically separate from each other. In such a case, the first portion and the second portion may be connected to each other to collectively form the casing. Optionally, the first portion and the second portion are connected using one of: a removable fastener, a non-removable fastener. Examples of the removable fastener include, a zipper, a slider, Velcro, a removable hinge, and the like. Examples of the non-removable fastener include, a non-removable hinge, an adhesive, a screw, and the like. Optionally, the casing is slidable.

The mattress is a flexible component that provides support and protection to the plurality of containers, whilst also facilitating in providing temperature regulation within the kit. Notably, the first part and the second part of the mattress is accommodated in the first portion and the second portion of the casing, respectively. Optionally, the mattress is welded to the casing. In this regard, at least a portion of the mattress, such as a middle portion of the mattress, may be welded to at least a part of the casing, such as a joint of the first portion and the second portion. It will be appreciated that other ways of joining the mattress to the casing are also well within the scope of the present disclosure. Optionally, a dimension and a shape of the first part and the second part of the mattress are such that they can be easily accommodated in the first portion and the second portion, respectively in a precise manner and snug fitted in the casing so as to avoid displacement and spillage of the refrigerant filled in the mattress. Examples of the refrigerant include, cold fluid, gel, or similar. Optionally, the predefined range of temperature is −5 degrees to −30 degrees Celsius. Alternatively, optionally, the predefined range of temperature is a range of temperature lying below a predefined temperature value, the predefined temperature value lying in a range of −5 degrees of Celsius to −60 degrees of Celsius. It is noteworthy that the temperature of the refrigerant lies within the predefined range of temperature, in order to enable in maintaining the temperature of the samples within the predefined range of temperature, when the kit is in the enclosed state. Moreover, when the temperature of the refrigerant lies within the predefined range of temperature, it may also enable in ensuring a snug fit of the plurality of containers in the plurality of cavities of the first type. Refrigerant is selected preferably such that it will experience phase transition from solid to liquid at temperatures lower than maximum storage temperature of samples which are stored and transported with the kit. As an example if the sample needs to be at temperature below −10 degrees Celsius then the refrigerant freezing point is selected to be −15 degrees Celsius for example.

A length of the mattress may be defined as a length of an edge extending in a direction along which the first part and the second part are arranged adjacently with respect to each other. As an example, the length of the mattress may be approximately 346 millimeters (mm). A width of the mattress may be 234 mm. A thickness of the mattress may be 6 mm when 0.3 liters of the refrigerant is filled in the mattress. A material used to manufacture the mattress has high durability, high strength, and has capacity to withstand low temperatures. Examples of the material of the mattress include, but are not limited to, plastic, rubber, acrylic, and silicone. In an example, the mattress may have frosted finish.

Notably, when the kit is in use, the mattress holds the refrigerant within itself. In an embodiment, the mattress is pre-filled with the refrigerant. In other words, the mattress is manufactured such that the first part and the second part of the mattress is filled with the refrigerant at a time of manufacturing. In another embodiment, the mattress is not filled with the refrigerant at a time of manufacturing, however, the refrigerant may be poured inside the mattress using suitable techniques, when the kit is in use.

It will be appreciated that the mattress is deformable (i.e., at least a portion of the first part and/or the second part of the mattress is capable of being deformed). This deformation capability of the mattress enables the mattress to rigidly encase or flexibly encase the stencil, as per requirement. The deformability of the mattress depends on the temperature of the refrigerant as the temperature of the refrigerant is same as the temperature of the mattress. Optionally, higher the temperature of the refrigerant, greater is the deformability of the mattress. For example, a deformability of the mattress when the temperature of the refrigerant is 0 degrees Celsius may be less than a deformability of the mattress when the temperature of the refrigerant is 10 degrees Celsius.

Technical effect of this is that there is no need to make special formations/openings/cavities/holes to the mattress during manufacturing. Indeed a "flat" type of matters can be used as an example.

An example use case: When the kit is taken in use the use sample containers are placed in the openings (or cavities/holes) of the first type of a stencil. The openings of the first type are dimensioned to receive containers (typically one container per opening). The refrigerant temperature is above freezing point of the refrigerant (in case of water above 0, in case of for example some cooling gel above say −5 degrees Celsius). Sample containers are pressed/placed to the openings of a first type of the stencil and therefore the containers will deform the mattress. The containers will form a cavity of a third type in the mattress. The cavity formfactor is thus defined by the container automatically.

After placing the containers the casing is closed and placed in freezer, at a temperature in which, the refrigerant experiences phase transition from liquid state to solid state (freezes in practice). Now the deformability of the mattress (due to low temperature) is lower or almost nonexistent. This way robust holding is ensured for the containers and also it is ensured that containers are firmly in contact with the matters to keep those in desired temperature.

Using deformable mattress material further enables to change the at least one stencil type to an other stencil type. As an example first used stencil type might have 10 cavities of a first type and other used stencil type might have 20 cavities of a first type or alternatively different type of cavities. This way the kit can be used to transport different formfactor of containers and different number of containers. The stencil might have several (such as 2, 3, 4, 5, 10) different type of openings dimensioned to receive several different type of containers.

Optionally, the mattress is elastic. In this regard, the mattress is made of an elastic material (i.e., a material which is capable of returning to its original shape and size after being deformed). Examples of the elastic material include, but are not limited to, rubber and some polymers.

In an embodiment, the first part and the second part of the mattress are separate from each other but are physically connected to each other. In this regard, the first part and the second part may be connected by a hinge part (in the form of a separate component that serves as a hinge, an edge between the first part and the second part, or similar), a flexible material, or similar.

Optionally, the mattress has a spout or opening that is resealable, and wherein the refrigerant is filled into the mattress and/or discharged out of the mattress, via the spout. Optionally, the spout or opening is provided on one of: the first part, the second part, of the mattress. The spout may be provided in a corner of the one of: the first part, the second part of the mattress. Optionally, the spout is covered using a cap. The cap prevents leakage of the refrigerant out of the mattress. Optionally, the mattress is filled with the refrigerant via the spout using any suitable technique known in the art. The spout is dimensioned to fit easily within the casing. Advantageously, the technical effect of the providing the spout is that the refrigerant can be filled inside the mattress and/or discharged out of the mattress with ease as per requirement of the user.

Optionally, the first part and the second part of the mattress are fluidically connected to each other via at least one bridge part of the mattress, and wherein when the kit is in use, the at least one bridge part holds the refrigerant therein. In this regard, a number of the at least one bridge part may depend upon the dimension of the first part and the second part of the mattress, a design of the first part and the second part, and the like. For example, larger the mattress, higher may be the number of the at least one bridge part which is provided to fluidically connect the first part and the second part of the mattress. This enables in quick filling/emptying of the refrigerant into/from the mattress. Optionally, the first part and the second part of the mattress are said to be "fluidically connected" to each other, when the refrigerant can pass from one of these parts to another of these parts through the at least one bridge part. As an example, when the mattress is folded, the refrigerant filled in one of the first part and the second part, may pass through the at least one bridge part to the other of the first part and the second part. Advantageously, the technical benefit of fluidically connecting the first part and the second part using the at least one bridge part is that the refrigerant can be easily and/or evenly distributed across the mattress, resulting in even temperature distribution across the mattress. Optionally, the at least one bridge part does not hold the refrigerant therein. In such a case, the at least one bridge part is not hollow and does not allow fluidic transmission of the refrigerant between different parts of the mattress.

Optionally, a given part of the mattress has a plurality of cavities of a third type, wherein the plurality of cavities of the third type are dimensioned and arranged throughout the given part, based on dimensions and an arrangement of the plurality of openings of the first type in the stencil. In this regard, the given part could be at least one of: the first part, the second part. Optionally, dimensions of the plurality of cavities of the third type are smaller than dimensions of at least one cavity of a second type (described later). Beneficially, the plurality of cavities of the third type are provided to enable the refrigerant held in the mattress to properly surround each of the plurality of containers held in the plurality of openings of the first type, whilst also ensuring a snug fit of the given part with the at least one stencil. In one embodiment the cavities of the third are formed during manufacturing to the mattress. In other embodiment the cavities of the third part are formed (as discussed earlier) when the container is placed/inserted in opening of the first type of the stencil. The term "cavity" encompasses both through-cavities (i.e., hollow cavities, which may also be understood to be openings), as well as non-hollow cavities such as a receptacle (which may be understood as a dent, a depression, a pit, or a well) in a material. Further more term "opening" and "cavity" might in some embodiments be interchangeable.

Next, the kit comprises the at least one stencil having the plurality of openings of the first type. In an embodiment, the kit comprises a single stencil. In another embodiment, the kit comprises a plurality of stencils. Optionally, when the kit comprises the plurality of stencils, the mattress also has at least one third part, the at least one third part being arranged between the first part and the second part, wherein a given stencil amongst the plurality of stencils is encased by any of: the first part and a given third part, the second part and a given third part, a given third part and another third part, when the kit is in the enclosed state. Optionally, the at least one stencil is made of at least one of: a Poly (methyl methacrylate) (PMMA) material, an acrylic material, a flexible material. In an example, the at least one stencil may have frosted finish. Optionally, a thickness of the at least one stencil lies within a range of 1 mm to 10 mm. As an example, the thickness of the at least one stencil may be 3 mm. The kit might comprise a first stencil having a first layout of openings and a second stencil having a second layout of openings.

Notably, the plurality of openings of the first type are dimensioned to receive the plurality of containers. In this regard, a shape of the plurality of openings may be in accordance with a shape of the plurality of containers. Further, a length and a width of the plurality of openings of the first type may be in accordance with a length and a width of the plurality of containers. Optionally, a number of the plurality of openings of the first type depends upon a dimension of the at least one stencil. As an example, in a stencil having a length of 234 mm and a width of 159 mm, the plurality of openings of the first type may be 16 in number. Optionally, the plurality of openings are formed by laser cutting. The laser cutting is used so as to facilitate precise cutting of the at least one stencil to obtain the plurality of openings of the first type.

Optionally, a material used to form the plurality of openings of the first type in the at least one stencil is one of: a rigid material, the flexible material. When the rigid material is used, the plurality of openings of the first type are rigidly-shaped receptacles, that are dimensioned to receive and securely accommodate the plurality of containers therein. When the flexible material is used, the flexible material deforms upon application of a force to yield flexible receptacles of the first type into which the plurality of containers can be accommodated, and upon removal of the force, the flexible material returns to its original form (for example, a planar form, a curved form, or similar). Optionally, when the flexible material is used to form the plurality of openings of the first type, and when the temperature of the refrigerant becomes such that the mattress expands (i.e., deforms), the flexible material returns to its original form.

In the original form of the flexible material, a corresponding opening of the first type is absent (i.e., not formed). In use, when the plurality of containers are put in their corresponding receiving places (i.e., the plurality of openings of the first type) in the at least one stencil, then said opening may keep the plurality of containers tightly-arranged in said receiving places, as long as the temperature of the refrigerant lies within the predefined range of temperature.

Notably, the plurality of containers are securely fitted in the plurality of openings of first type when the kit is in use. Optionally, when the kit comprises the plurality of containers, the plurality of containers are fitted in the plurality of openings of the first type during manufacturing of the at least one stencil. Optionally, the plurality of containers comprise at least two of: a vial, a microcentrifuge tube, a test tube that is fluidically sealable, a vacutainer, a drug bottle. Optionally, the plurality of containers have different shapes, different volumes, different materials. Notably, each of the plurality of containers is closed at the first end. Optionally, the first end is closed using a cap. Optionally, the cap is implemented as one of: a screw cap, a snap cap, a flange plug cap, a plug stopper cap. Optionally, a given container is implemented as an Eppendorf tube. As an example, the plurality of container may be Eppendorf tubes, wherein each of the Eppendorf tubes may have volume of 2 ml. The term "encased" refers to a state in which the at least one stencil is placed between the first part and the second part of the mattress. Notably, the at least one stencil is encased between the first part and the second part, when the kit is in the enclosed state. When the kit is in an open state, the at least one stencil rests on any of the first part and the second part. Encasing of the at least one stencil between the first part and the second part results in proper coverage of the plurality of containers with the refrigerant filled in the mattress. Therefore, the temperature of the samples in the plurality of containers is maintained within the predefined range of temperature.

Optionally, the at least one stencil further comprises at least one opening of a second type, and wherein the at least one opening of the second type, in use, holds at least one sensor therein, the at least one sensor being implemented as at least one of: a temperature sensor, a motion sensor, a proximity sensor. In this regard, the at least one opening of the second type may have a shape and size that is suitable to adequately and securely hold the at least one sensor. As an example, the at least one opening of the third type has a circular shape. Optionally, the at least one opening of the second type is formed by the laser cutting. Optionally, the at least one sensor is arranged in a housing, and the at least one opening of the second type is used to hold the housing therein.

One or more openings may also be arranged to provide a place for containers for third type of storage function, such as spare containers for the type one etc.

Optionally, the temperature sensor, in operation, generates sensor data indicative of a temperature in the closed space between the first portion and the second portion of the casing, the temperature sensor being communicably coupled to a processor, and wherein the processor is configured to determine whether the temperature in the closed space lies outside the predefined range of temperature, and generate an indication indicative of an anomalous temperature condition when it is determined that the temperature in the closed space lies outside the predefined range of temperature. In this regard, optionally, the processor could be a part of the kit, or be external to the kit (for example, as a processor of a device of a person carrying the kit, a cloud processor, or similar). Optionally, the temperature sensor is communicably coupled to the processor via the communication network. Optionally, the temperature sensor detects the temperature in the closed space between the first part and the second part of the casing and sends the sensor data to the processor. Upon receiving the sensor data, the processor compares the sensor data with the predefined range of temperature. When it is determined that the temperature in the closed space is outside the predefined range of temperature, the processor generates the indication. Optionally, the indication is provided by at least one indicator, so the processor sends a control signal to the at least one indicator to indicate the anomalous temperature condition. As an example, the predefined range of temperature may be −10 degree Celsius to −20 degree Celsius and the temperature of the closed space may be +10 degree Celsius, in such as a case, the processer may generate the indication. In case of the anomalous temperature condition, the mattress of the kit may be replaced, or filled with a new refrigerant, or similar. Advantageously, the technical effect of employing the temperature sensor in the kit is that the anomalous temperature conditions can be easily and timely detected, and subsequently rectified.

Optionally, the sensor may also have a memory to store temperature values and also other values such as acceleration or movement to detect possible mishandling; therefore the history of the kit can be read and the decisions concerning the validity of contents can be further assessed. The assessment may lead into actions: instructing user further, make decisions on the usage of the contents etc.

Optionally, the proximity sensor, in operation, generates sensor data indicative of distances of the plurality of containers from the proximity sensor, the proximity sensor being communicably coupled to a processor, and wherein the processor is configured to determine whether a given container is removed from its corresponding opening of the first type, based on the sensor data and pre-known distances of the proximity sensor from the plurality of openings of the first type, and generate at least an indication indicative of removal of the given container from its corresponding opening of the first type, when it is determined that the given container is removed from its corresponding opening of the first type. In this regard, optionally, the processor could be a part of the kit, or be external to the kit (for example, as a processor of a device of a person carrying the kit, a cloud processor, or similar). Optionally, the proximity sensor is communicably coupled to the processor via the communication network. Optionally, the proximity sensor detects distances of the plurality of containers from the proximity sensor and sends the sensor data to the processor. Upon receiving the sensor data, the processor compares the sensor data with the pre-known distances of the proximity sensor from the plurality of openings of the first type. Optionally, the pre-known distances of the proximity sensor are known by specification during manufacturing of the kit. When a distance of a given container from the proximity sensor is different from the pre-known distances, the processor generates the indication. Optionally, the indication is provided by the at least one indicator, so the processor sends a control signal to the at least one indicator to indicate the removal of at least one container. Optionally, the processor is configured to also generate an indication indicative of placement of a given container in its corresponding opening of the first type. Advantageously, the technical effect of this is that a timeline of removal of the plurality of containers can be maintained with ease. Further example of detecting removal and insertion of one or more containers might include electrical conductivity from one edge of a opening of the first type to an other edge. The container would close the electrical circuit to generate signal when the container is in place (and non-signal when it is removed).

Optionally, furthermore, if the sensor is coupled with mobile device, the location of said sensor and kit thereof can be assessed; information therefore can be utilized in providing further services, instructions for completing context awareness.

Optionally, wherein the motion sensor, in operation, generates sensor data indicative of motion of the kit, the motion sensor being communicably coupled to a processor, and wherein the processor is configured to determine whether the motion of the kit exceeds a predefined threshold value, and generate an indication indicative of an anomalous motion condition when it is determined that the motion of the kit exceeds the predefined threshold value. In this regard, optionally, the processor could be a part of the kit, or be external to the kit (for example, as a processor of a device of a person carrying the kit, a cloud processor, or similar). Optionally, the motion sensor is communicably coupled to the processor via the communication network. The motion may be imparted to the kit during transportation of the kit, during storage of the kit, or similar. Optionally, the motion sensor detects the motion of the kit along various coordinate axis, and the sensor data is sent to the processor via the communication network. The motion sensor could be a 3 degrees of freedom (DoF) motion sensor, a 6 DoF motion sensor, or similar. Examples of the motion sensor include, an accelerometer, a gyroscope, an inertial measurement unit (IMU), and the like. The processor compares the sensor data with the predefined threshold value. When it is detected that the motion of the kit exceeds the predefined threshold value, the processor generates the indication. Optionally, the indication is provided by at least one indicator, so the processor sends a control signal to the at least one indicator to indicate the anomalous motion condition of the kit. It is crucial to keep in check the anomalous motion condition so as to avoid problems related with displacement of the plurality of container in the kit. As an example, the predefined threshold value may be 1 $m/s^2$ and the acceleration value of the kit during transportation may be 1.3 $m/s^2$. In such a case, the processor may generate the indication. Advantageously, the technical effect of employing the motion sensor is timely detection of the anomalous motion condition.

Optionally, the kit further comprises the processor. In this regard, the processor is arranged in the kit, and thus a person carrying/using the kit need not use any other device for monitoring operating conditions of the kit. Throughout the present disclosure, the term "processor" refers to a computational element that is operable to respond to and process instructions. Furthermore, the term "processor" may refer to one or more individual processors, processing devices and various elements associated with a processing device that may be shared by other processing devices. Such processors, processing devices and elements may be arranged in various architectures for responding to and executing processing steps.

Optionally, the kit further comprises at least one indicator arranged on at least one of: the casing, the at least one stencil, the at least one indicator being coupled to a processor, and wherein the at least one indicator is at least one of: a light-emitting element, a sound-emitting element, a haptic element. In this regard, the at least one indicator is communicably coupled to the processor via a communication network. It will be appreciated that the communication network may be wired, wireless, or a combination thereof. The communication network could be an individual network or a combination of multiple networks. Examples of the communication network may include, but are not limited to one or more of, Internet, a local network (such as, a TCP/IP-based network, an Ethernet-based local area network, an Ethernet-based personal area network, a Wi-Fi network, and the like), Wide Area Networks (WANs), Metropolitan Area Networks (MANs), a telecommunication network, and a short-range radio network (such as Bluetooth®). Optionally, the at least one indicator is provided on the kit such that an indication provided by the at least one indicator can be conveniently perceived by a user. The light-emitting element provides a visual indication. The sound-emitting element provides an audio indication. The haptic element provides a haptic (i.e., touch-based) indication. In one example, the at least one indicator may be provided on the casing. In another example, the at least one indicator may be provided on the at least one stencil. In yet another example, the at least one indicator may be provided on the casing and on the at least one stencil. Examples of the light-emitting element include, but are not limited to, a Light-Emitting Diode (LED), and a display. Examples of the sound-emitting element include, but are not limited to, a buzzer, a loudspeaker. As an example, in case of the anomalous temperature condition, the at least one indicator may give red light. As another example, in case of the anomalous motion condition, the at least one indicator may give a sound. It will be appreciated that more than one indications may be generated in case of various anomalous operating conditions. Advantageously, the technical effect of the at least one indicator is that the anomalous operating conditions of the kit are not gone unnoticed since the at least one indicator provides the indication of the same, and therefore such anomalous operating conditions can be acted upon timely, resulting in avoiding any damage to the samples kept in the kit.

Also, optionally the indicator may be built by using mobile device in the proximity and the plurable options of such device, Optionally, the kit further comprises a plurality of holders for the plurality of containers, wherein a given holder is arranged on a second end of a corresponding container to facilitate detachment or attachment of said container in a corresponding opening of the first type, and wherein said opening of the first type is dimensioned to receive an arrangement of the given holder with its corresponding container therein and to hold said arrangement securely. A material used to manufacture the plurality of holders has enhanced flexibility, enhanced strength, and high durability. Examples of the material of the plurality of holders include, but are not limited to, Thermoplastic Polyurethanes (TPU), Polyester, Polyether and Polycaprolactone. In an example, the plurality of holders may have matte finish. The plurality of holders are dimensioned such that they can be tightly as well as easily arranged on the second end of the plurality of containers. Advantageously, the technical effect of arranging a given holder on a given container is that the given container can be easily placed or removed from the at least one stencil without any damage to the at least one stencil or the given container.

Optionally, the kit further comprises at least one plate arranged between a given portion of the casing and a corresponding part of the mattress, wherein the at least one plate is capable of holding at least one of: the refrigerant, a sample held in a given container, upon leakage thereof. Optionally, the given portion of the casing is at least one of: the first portion, the second portion. In case the given portion is the first portion, the at least one plate is arranged between the first portion and the first part of the mattress. In case the given portion is the second portion, the at least one plate is arranged between the second portion and the second part of the mattress. Optionally, a number of the at least one plate depends upon the number of the at least one stencil. The at least one plate has good absorbing capacity so as to adequately absorb the at least one of: the refrigerant, the sample held in the given container. Examples of a material of the at least one plate include, but are not limited to, a fabric or cotton. Optionally, dimensions of the at least one plate are such that it can be precisely and snugly arranged between the given portion of the casing and the corresponding part of the mattress. Advantageously, the technical effect of the at least one plate is that the at least one of: the refrigerant, a sample held in a given container is easily collected, upon leakage thereof.

Optionally, the kit further comprises at least one three-part mounting pin, wherein the given part and the at least one stencil comprise at least one set of through-holes, and wherein the at least one three-part mounting pin, in use, is arranged to pass through the at least one set of through-holes for securing an arrangement of the at least one stencil, a given part of the mattress upon which the at least one stencil would rest when the kit is in an open state, and a given portion of the casing corresponding to the given part. The at least one three-part mounting pin has three parts which passes through through-holes for secured arrangement of the at least one stencil, the corresponding part of the mattress and the corresponding portion of the casing. In this regard, optionally, the kit comprises four three-part mounting pins. The four three-part mounting pins may pass through four sets of through-holes. In an example, each of the four three-part mounting pins may pass through the at least one stencil, the first part of the mattress and the first portion of the casing. Advantageously, the technical effect of this is that slippage/drifting of the at least one stencil and/or the mattress with respect to each other when using the kit is minimized.

Optionally, the kit further comprises a lock, wherein when the kit is in use, the lock is operable to open and to securely close the first portion and the second portion with respect to each other, for attaining an open state and the enclosed state of the kit, respectively. In this regard, the term "lock" refers to an element that is used for opening or securely closing the first portion and the second portion of the casing. Optionally, the lock is provided on the casing. Optionally, the lock is integrated with the casing. Optionally, the lock is a separate element that is detachably attached with the casing. Optionally, the lock has a movable locking mechanism. Advantageously, the technical effect of the lock is that the kit may be maintained in the open state or the enclosed state with ease.

Optionally, visual indicators indicative of a correct manner of positioning the plurality of containers in the plurality of openings of the first type are provided on at least one of: the at least one stencil, the mattress, the plurality of containers. In this regard, the visual indicators are in the form of at least one of alphabetic codes, numeric codes, quick response (QR) codes, colouring, geometric designs (such as lines, shapes, patterns, and similar), and the like. In this regard, the phrase "correct manner of positioning" refers to proper orientation of the plurality of containers in the plurality of openings of first type. In an implementation, the visual indicators may be provided on the at least one stencil. In this regard, the visual indicators may be provided in proximity to each of the plurality of openings of the first type. Herein, the visual indicator may represent a timeline for collecting samples in each of the plurality of containers to be received in the plurality of openings of first type. As an example, the visual indicators may represent timelines such as evening 1, evening 2, or similar for each of the plurality of openings of first type representing when samples have to be taken and put in a given container of a corresponding opening of first type. In another implementation, the visual indicators may be provided on each of the plurality of containers. In this regard, the visual indicators may indicate information of the samples held in the plurality of containers.

Optionally, said visual indicators (cues) may also be utilized as: the instructions for a user to follow certain pre-defined protocols or regimens, comprising of at least one use of a container, and easily recognize the correct order and/or timing thereof; said regimen may also be presented, along with physical placement with digitally comprised instructions, supported with QR- or bar-code or proximity sensor or scanning otherwise, for example, to provide digital instructions for the order, timing or qualitative means.

DETAILED DESCRIPTION OF THE DRAWINGS

Referring to FIG. 1, illustrated is an exploded view of a kit 100 for holding samples, in accordance with an embodiment of the present disclosure. The kit 100 comprises a casing 102 having a first portion 102*a* and a second portion 102*b*, wherein when the kit is in an enclosed state (not shown), the first portion 102*a* and the second portion 102*b* define a closed space therebetween. Next the kit 100 comprises a mattress 104 having at least a first part 104*a* and a second part 104*b*, wherein the first part 104*a* and the second part 104*b* of the mattress 104 are accommodated in the first portion 102*a* and the second portion 102*b* of the casing 102, respectively. Next, the kit 100 comprises at least one stencil (depicted as a stencil 106) having a plurality of openings of a first type (depicted for example as openings 108 of first type), wherein the openings 108 of first type are dimensioned to receive a plurality of containers (depicted for example as containers 110) therein and to hold the plurality of containers 110 securely. Each container being capable of holding a sample therein and being closed at its first end (depicted for example as first ends 112), wherein when the kit is in the enclosed state (not shown), the stencil 106 is encased by the first part 104*a* and the second part 104*b*, thereby enabling a temperature of the samples (not shown) held in the containers 110 to be maintained within the predefined range of temperature. The containers 110 also has a second end 114. When the containers 110 are inserted into the openings of the first type those will be (when the case is closed) in contact with a surface of mattress. Indeed the first portion 104*a* will be in contact of a first side of the container and the second portion 104*b* will be in contact with a second side of the container. The containers 110 presses the surfaces of the mattress with a force F, thus forming there (in one embodiment) a plurality of cavities of a third type 105 (by deformation of the mattress). In alternative/additional embodiment the plurality of cavities of the third types are formed in the mattress during manufacturing.

Figure 2:
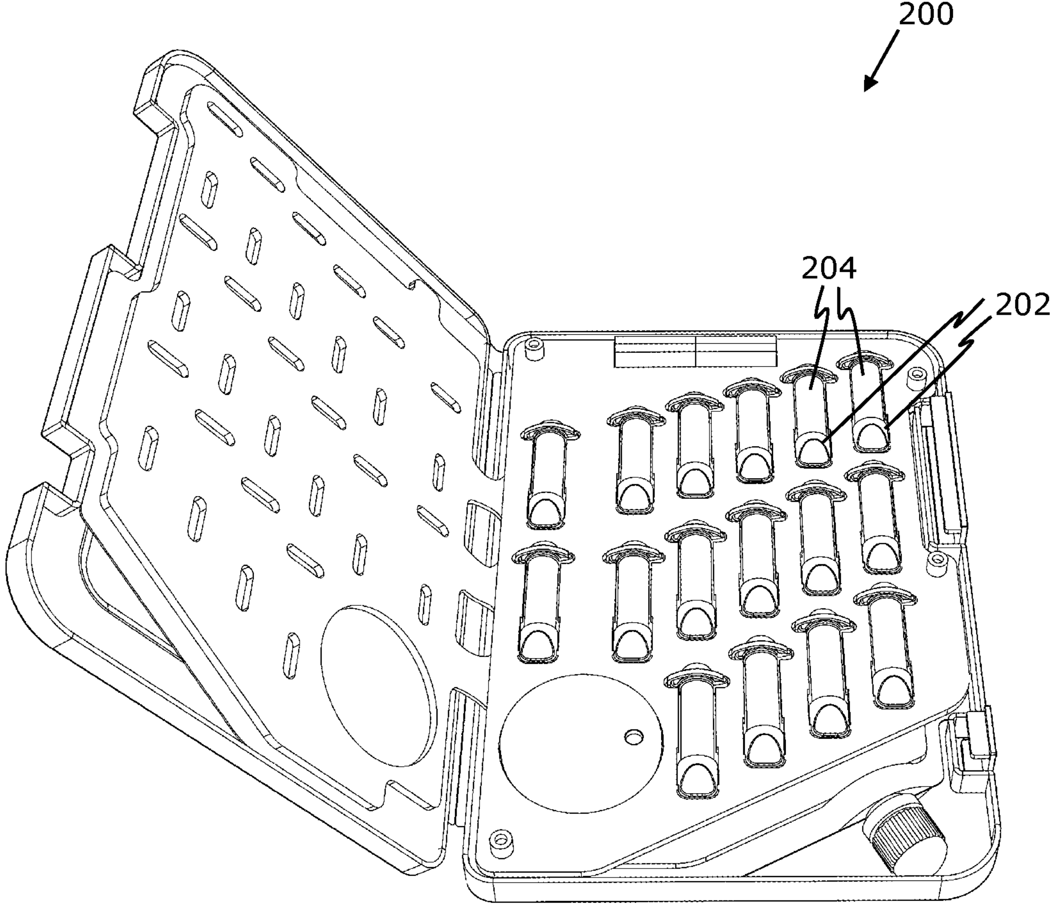
FIG. 2 is schematic illustration of a kit for holding samples, wherein the kit is in an open state, in accordance with an embodiment of the present disclosure.

Referring to FIG. 2, illustrated is a schematic illustration of a kit for holding samples, wherein the kit is in an open state, in accordance with an embodiment of the present disclosure. The kit 200 comprises a plurality of holders (depicted for example as holders 202) for the plurality of containers (depicted for example as containers 204), wherein the holders 202, are arranged on a second end of corresponding containers 204, to facilitate detachment or attachment of the containers 204 in corresponding openings of first type.

Figure 3:
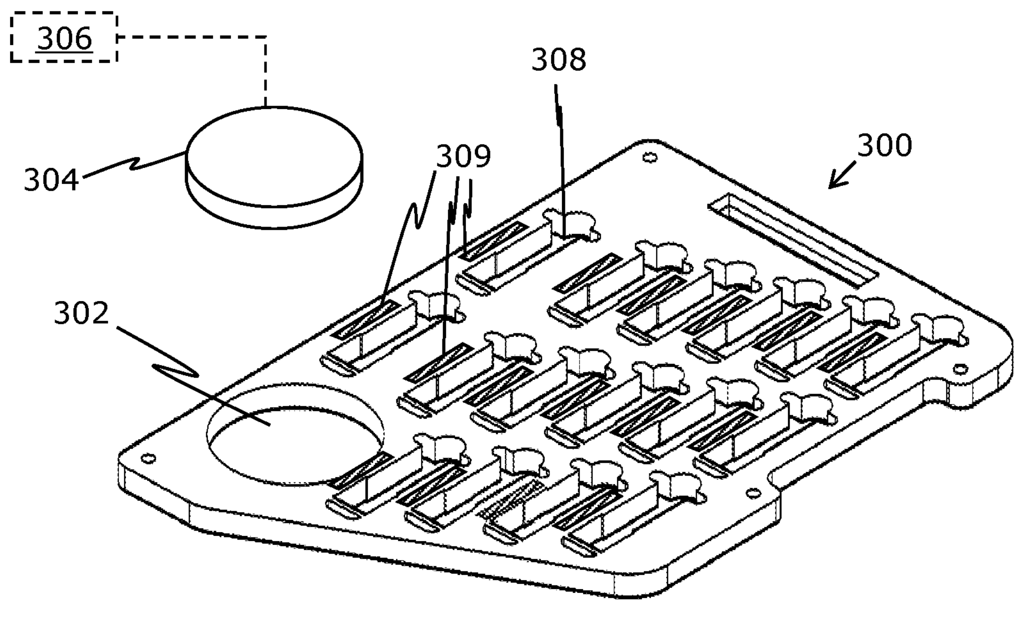
FIG. 3 is a schematic illustration of at least one stencil, in accordance with an embodiment of the present disclosure.

Referring to FIG. 3, illustrated is a schematic illustration of at least one stencil (depicted for example as a stencil 300), in accordance with an embodiment of the present disclosure. The stencil 300 comprises an opening 302 of second type, and wherein the opening 302 of the second type in use, holds at least one sensor (depicted for example as a sensor 304) therein. The stencil comprises a plurality of openings 308 of a first type for receiving containers. The sensor 304 is communicably coupled to a processor 306. Further, at least one indicator (depicted for example as indicators 309) is arranged on the stencil 300.

Figure 4:
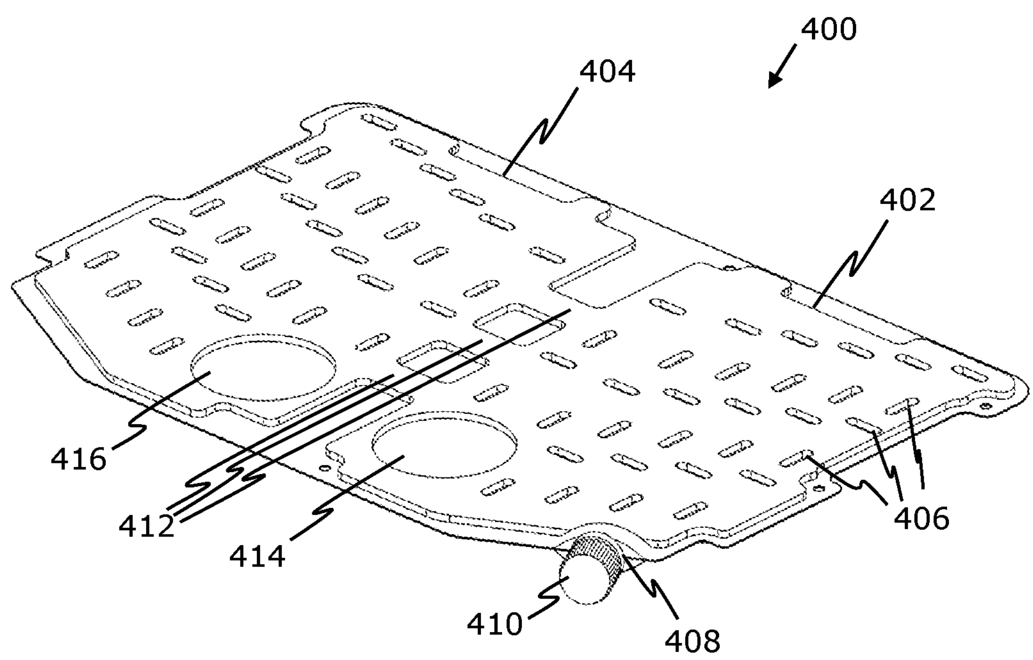
FIG. 4 is a schematic illustration of a mattress, in accordance with an embodiment of the present disclosure.

Referring to FIG. 4, illustrated is a schematic illustration of a mattress 400, in accordance with an embodiment of the present disclosure. The mattress 400 has a first part 402 and a second part 404. Each of the first part 402 and the second part 404 has a plurality of cavities of a third type (depicted for example as cavities 406 of third type). The first part 402 also has a spout 408 that is resealable, using a cap 410 and wherein a refrigerant is filled into the mattress 400 and/or discharged out of the mattress 400, via the spout 408. The first part 402 and the second part 404 of the mattress 400 are fluidically connected to each other via at least one bridge part (depicted for example as bridge parts 412) of the mattress 400. Further, each of the first part 402 and the second part 404 of the mattress comprises cavities 414 and 416, respectively corresponding to at least one cavity of second type of the at least one stencil (not shown).

Figure 5:
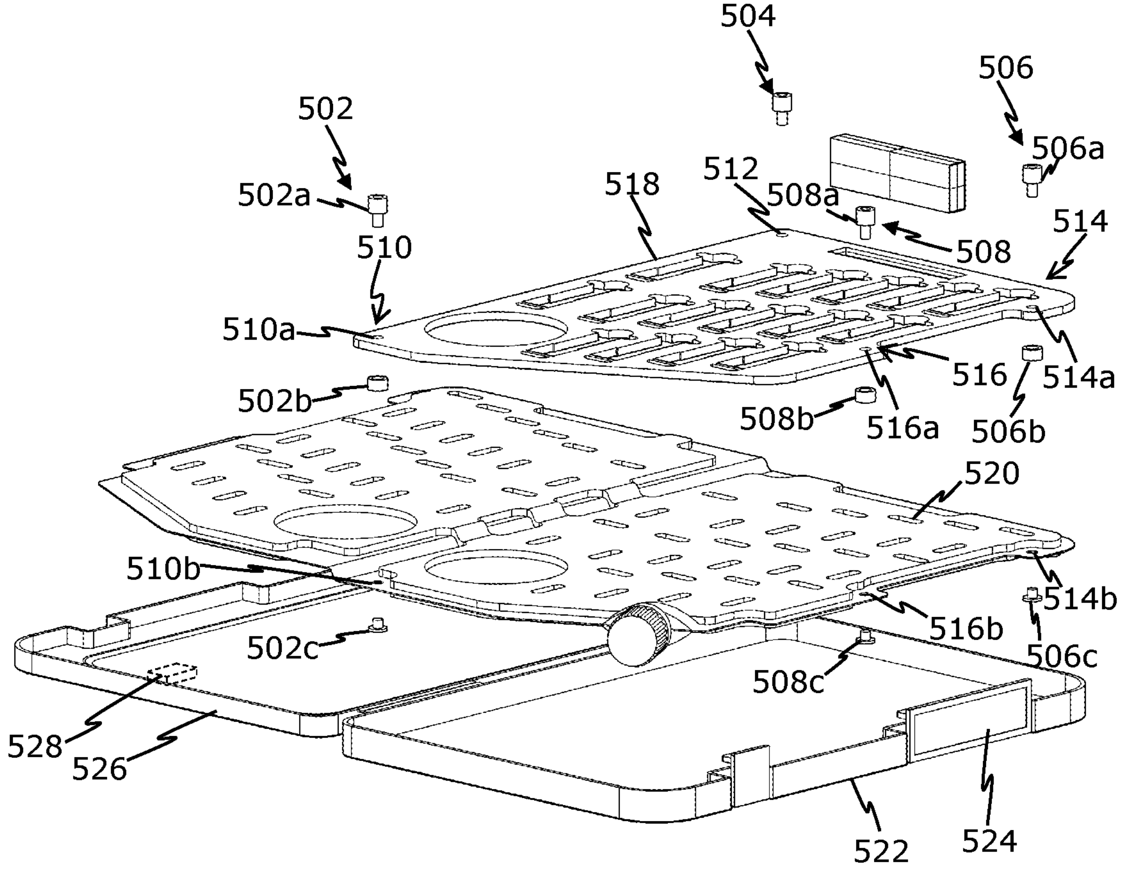
FIG. 5 is an exploded view representing how at least one three-part mounting pin is arranged in a kit for holding samples, in accordance with an embodiment of the present disclosure.

Referring to FIG. 5, illustrated is an exploded view representing how at least one three-part mounting pin (depicted for example, as four three-part mounting pins 502, 504, 506 and 508) is arranged in a kit for holding samples, in accordance with an embodiment of the present disclosure. Each of the three-part mounting pins 502, 504, 506 and 508 has three sub-parts. For example, the three-part mounting pin 502 has three sub-parts 502*a*, 502*b*, and 502*c*. Sub-parts of the three-part mounting pin 504 are invisible form this perspective. The three-part mounting pin 506 has three sub-parts 506*a*, 506*b*, and 506*c*. The three-part mounting pin 508 has three sub-parts 508*a*, 508*b*, and 508*c*. The mounting pins 502, 504, 506 and 508, in use, are arranged to pass through at least one set of through-holes (depicted for example as four sets of through-holes 510, 512, 514, and 516) for securing an arrangement of the stencil 518, a first part 520 of a mattress and a first portion 522 of a casing. Each of the four sets of through-holes 510, 512, 514, and 516 comprises holes (depicted for example as holes 510*a*, 510*b*, 514*a*, 514*b*, 516*a*, 516*b*) in each of the stencil 518 and the mattress 520. Holes corresponding to the mounting pin 504 in the first part 520 of the mattress is invisible from this perspective. Further, the kit comprises a lock (depicted for example as a lock 524) that is operable to open and to securely close a first portion 522 and the second portion 526 with respect to each other, for attaining an open state and the enclosed state of the kit, respectively. The kit further comprises at least one indicator (depicted for example as an indicator 528) arranged on the second portion 526 of the casing.

FIGS. 1, 2, 3, 4, and 5 are merely examples, which should not unduly limit the scope of the claims herein. A person skilled in the art will recognize many variations, alternatives, and modifications of embodiments of the present disclosure.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A kit for holding samples, the kit comprising:

a casing having a first portion and a second portion, wherein when the kit is in an enclosed state, the first portion and the second portion define a closed space therebetween;

a mattress having at least a first part and a second part, wherein the first part and the second part of the mattress are accommodated in the first portion and the second portion of the casing, respectively, wherein when the kit is in use, the mattress holds a refrigerant therein, a temperature of the refrigerant lies within a predefined range of temperature, and wherein the mattress is deformable such that its deformability depends on the temperature of the refrigerant;

at least one stencil having a plurality of openings of a first type, wherein the plurality of openings of the first type are dimensioned to receive a plurality of containers therein and to hold the plurality of containers securely, each container being capable of holding a sample therein and being closed at its first end, wherein when the kit is in the enclosed state, the at least one stencil is encased by the first part and the second part, thereby enabling a temperature of the samples held in the plurality of containers to be maintained within the predefined range of temperature; and at least one three-part mounting pin, wherein the given part and the at least one stencil comprise at least one set of through-holes, and wherein the at least one three-part mounting pin, in use, is arranged to pass through the at least one set of through-holes for securing an arrangement of the at least one stencil, a given part of the mattress upon which the at least one stencil would rest when the kit is in an open state, and a given portion of the casing corresponding to the given part.

2. The kit according to claim 1, further comprising a plurality of holders for the plurality of containers, wherein a given holder is arranged on a second end of a corresponding container to facilitate detachment or attachment of said container in a corresponding opening of the first type, and wherein said opening of the first type is dimensioned to receive an arrangement of the given holder with its corresponding container therein and to hold said arrangement securely.

3. The kit according to claim 1, further comprising at least one plate arranged between a given portion of the casing and a corresponding part of the mattress, wherein the at least one plate is capable of holding at least one of: the refrigerant, a sample held in a given container, upon leakage thereof.

4. The kit according to claim 1, further comprising a lock, wherein when the kit is in use, the lock is operable to open and to securely close the first portion and the second portion with respect to each other, for attaining an open state and the enclosed state of the kit, respectively.

5. The kit according to claim 1, wherein visual indicators indicative of a correct manner of positioning the plurality of containers in the plurality of openings of the first type are provided on at least one of: the at least one stencil, the mattress, the plurality of containers.

6. The kit according to claim 1, wherein the at least one stencil further comprises at least one opening of a second type, and wherein the at least one opening of the second type, in use, holds at least one sensor therein, the at least one sensor being implemented as at least one of: a temperature sensor, a motion sensor, a proximity sensor.

7. The kit according to claim 6, wherein the temperature sensor, in operation, generates sensor data indicative of a temperature in the closed space between the first portion and the second portion of the casing, the temperature sensor being communicably coupled to a processor, and wherein the processor is configured to determine whether the temperature in the closed space lies outside the predefined range of temperature, and generate an indication indicative of an anomalous temperature condition when it is determined that the temperature in the closed space lies outside the predefined range of temperature.

8. The kit according to claim 6, wherein the proximity sensor, in operation, generates sensor data indicative of distances of the plurality of containers from the proximity sensor, the proximity sensor being communicably coupled to a processor, and wherein the processor is configured to determine whether a given container is removed from its corresponding opening of the first type, based on the sensor data and pre-known distances of the proximity sensor from the plurality of openings of the first type, and generate at least an indication indicative of removal of the given container from its corresponding opening of the first type, when it is determined that the given container is removed from its corresponding opening of the first type.

9. The kit according to claim 6, wherein the motion sensor, in operation, generates sensor data indicative of motion of the kit, the motion sensor being communicably coupled to a processor, and wherein the processor is configured to determine whether the motion of the kit exceeds a predefined threshold value, and generate an indication indicative of an anomalous motion condition when it is determined that the motion of the kit exceeds the predefined threshold value.

10. The kit according to claim 7, wherein the kit further comprises the processor.

11. The kit according to claim 1, wherein the kit further comprises at least one indicator arranged on at least one of: the casing, the at least one stencil, the at least one indicator being coupled to a processor, and wherein the at least one indicator is at least one of: a light-emitting element, a sound-emitting element, a haptic element.

12. The kit according to claim 1, wherein the mattress has a spout or opening that is resealable, and wherein the refrigerant is filled into the mattress and/or discharged out of the mattress, via the spout.

13. The kit according to claim 1, wherein the first part and the second part of the mattress are fluidically connected to each other via at least one bridge part of the mattress, and wherein when the kit is in use, the at least one bridge part holds the refrigerant therein.

14. The kit according to claim 1, wherein a given part of the mattress has a plurality of cavities of a third type, wherein the plurality of cavities of the third type are dimensioned and arranged throughout the given part, based on dimensions and an arrangement of the plurality of openings of the first type.

15. A kit for holding samples, the kit comprising:

a casing having a first portion and a second portion, wherein when the kit is in an enclosed state, the first portion and the second portion define a closed space therebetween;

a mattress having at least a first part and a second part, wherein the first part and the second part of the mattress are accommodated in the first portion and the second portion of the casing, respectively, wherein when the kit is in use, the mattress holds a refrigerant therein, a temperature of the refrigerant lies within a predefined range of temperature, and wherein the mattress is deformable such that its deformability depends on the temperature of the refrigerant; and at least one stencil having a plurality of openings of a first type, wherein the plurality of openings of the first type are dimensioned to receive a plurality of containers therein and to hold the plurality of containers securely, each container being capable of holding a sample therein and being closed at its first end, wherein when the kit is in the enclosed state, the at least one stencil is encased by the first part and the second part, thereby enabling a temperature of the samples held in the plurality of containers to be maintained within the predefined range of temperature, wherein a given part of the mattress has a plurality of cavities of a third type, and wherein the plurality of cavities of the third type are dimensioned and arranged throughout the given part, based on dimensions and an arrangement of the plurality of openings of the first type.

* * * * *